US012758771B2

(12) United States Patent
Wasserman et al.

(10) Patent No.: US 12,758,771 B2
(45) Date of Patent: *Oct. 13, 2026

(54) DEVICES, SYSTEMS, AND METHODS FOR APPLYING TUMOR-TREATING FIELDS

(71) Applicant: NOVOCURE GMBH, Root (CH)

(72) Inventors: Yoram Wasserman, Haifa (IL); Stas Obuchovsky, Haifa (IL); Nataliya Kuplennik, Haifa (IL); David Shapiro, Haifa (IL)

(73) Assignee: NOVOCURE GMBH, Baar (CH)

( * ) Notice: Subject to any disclaimer, the term of this patent is extended or adjusted under 35 U.S.C. 154(b) by 388 days.

This patent is subject to a terminal disclaimer.

(21) Appl. No.: 18/193,923

(22) Filed: Mar. 31, 2023

(65) Prior Publication Data

US 2023/0310850 A1 Oct. 5, 2023

Related U.S. Application Data

(60) Provisional application No. 63/326,066, filed on Mar. 31, 2022.

(51) Int. Cl.
*A61N 1/36* (2006.01)
*A61N 1/04* (2006.01)

(52) U.S. Cl.
CPC ....... *A61N 1/36002* (2017.08); *A61N 1/0476* (2013.01); *A61N 1/0496* (2013.01); *A61N 1/36014* (2013.01)

(58) Field of Classification Search
CPC .. A61N 1/04; A61N 1/36002; A61N 1/36048; A61N 1/0456; A61N 1/0468
See application file for complete search history.

(56) References Cited

U.S. PATENT DOCUMENTS

2021/0052884 A1* 2/2021 Jashek ................ A61N 1/0456

* cited by examiner

*Primary Examiner* — Alyssa M Alter
(74) *Attorney, Agent, or Firm* — Ballard Spahr LLP

(57) ABSTRACT

Assemblies for use in applying TTFields are disclosed. A treatment assembly can include a circuit board, a plurality of electrode elements, and a cover. Each electrode element of the plurality of electrode elements can have a metal layer and, optionally, a capacitive layer. Each electrode element can be coupled to the circuit board via the metal layer of the electrode element. At least a first electrode element of the plurality of electrode elements can be positioned on an outer side of the circuit board. A first portion of the cover can be disposed over the first electrode element and the outer side of the circuit board, and the first portion can contact the first electrode. A second portion of the cover can be positioned radially outside of a perimeter of the circuit board. The cover can include a layer of anisotropic material and at least one conductive adhesive or gel layer.

20 Claims, 5 Drawing Sheets

DEVICES, SYSTEMS, AND METHODS FOR APPLYING TUMOR-TREATING FIELDS

CROSS-REFERENCE TO RELATED APPLICATION

This application claims priority to, and the benefit of the filing date of, U.S. Provisional Application No. 63/326,066, filed Mar. 31, 2022, the entirety of which is hereby incorporated by reference herein.

BACKGROUND

Tumor Treating Fields (TTFields) therapy is a proven approach for treating tumors using alternating electric fields at frequencies between 50 KHz-1 MHz, such as, for example, 100-500 kHz. The alternating electric fields are induced by electrode assemblies (e.g., arrays of capacitively coupled electrodes, also called transducer arrays) placed on opposite sides of a target location in the subject's body. When an AC voltage is applied between opposing electrode assemblies, an AC current is coupled through the electrode assemblies and into the subject's body. And higher currents are strongly correlated with higher efficacy of treatment.

The electrode assemblies used during application of TTFields typically include metal (metallization) elements that are in electrical communication with a source of voltage (e.g., through a circuit board) and dielectric (e.g., ceramic) elements that face toward the skin of a patient. Often, the dielectric elements are separated from the skin by only soft adhesive material (e.g., hydrogel) that directly contacts the skin. This positioning of the dielectric elements can lead to increased heating and slow cooling of the skin. Further, the concentrated current at the interfaces between the dielectric elements and the soft adhesive material can lead to inconsistent heating and/or current throughout the footprint of the treatment apparatus, with the potential to cause localized heating and/or current spikes. In order to address these inconsistencies in heating and/or current, there have been attempts to use large printed circuit boards, which can support an increased number of dielectric elements across a wider footprint. However, the use of such large circuit boards results in a larger footprint for the treatment apparatus, leading to increased rigidity (and reduced flexibility).

SUMMARY

Disclosed herein, in various aspects, are treatment assemblies for use in applying TTFields. In one exemplary aspect, a treatment assembly can include a circuit board, a plurality of electrode elements, and a cover. The circuit board can have a skin-facing side and an opposing outer side. The circuit board can have a perimeter. Each electrode element of the plurality of electrode elements can have a metal layer and, optionally, a capacitive layer. Each electrode element can be coupled to the circuit board via the metal layer of the electrode element. At least a first electrode element of the plurality of electrode elements can be positioned on the outer side of the circuit board. The cover has a first portion and a second portion. The first portion is disposed over the first electrode element and the outer side of the circuit board, and the first portion contacts the first electrode element. The second portion is positioned radially outside of the perimeter of the circuit board. The cover can include a layer of anisotropic material and at least one conductive adhesive or gel layer. Any contact between the cover and an electrode element of the plurality of electrode elements occurs by contact with a conductive adhesive or gel layer of the at least one conductive adhesive or gel layer. The layer of anisotropic material comprises a sheet of anisotropic material having a front face (that faces the skin) and a rear face (that faces away from the skin), the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, wherein resistance of the sheet in directions that are parallel to the front face is less than half of the first resistance.

In another exemplary aspect, the treatment assembly includes a plurality of electrode elements, a cover, a base structure, and a thermal barrier layer. The plurality of electrode elements each include a metal layer. The cover has a first portion and a second portion. The first portion is disposed over the plurality of electrode elements, and the first portion of the cover has a skin-facing side that contacts at least a first electrode element of the plurality of electrode elements. The second portion is positioned outwardly beyond the area occupied by the plurality of electrode elements. The cover includes a layer of anisotropic material and at least one conductive adhesive or gel layer. Any contact between the cover and an electrode element of the plurality of electrode elements occurs by contact with a conductive adhesive or gel layer of the at least one conductive adhesive or gel layer of the cover. The base structure is positioned on the skin-facing side of the first portion of the cover such that the first portion of the cover overlies the base structure. The base structure includes a second layer of anisotropic material and at least one conductive adhesive or gel layer. The thermal barrier layer is positioned between the base structure and the first electrode element. The layer of anisotropic material and the second layer of anisotropic material each comprise a respective sheet of anisotropic material having a front face (that faces the skin) and a rear face (that faces away from the skin), the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, wherein resistance of the sheet in directions that are parallel to the front face is less than half of the first resistance.

Systems and methods for using the disclosed treatment assemblies are also disclosed.

BRIEF DESCRIPTION OF THE DRAWINGS

Various embodiments are described in detail below with reference to the accompanying drawings, wherein like reference numerals represent like elements.

DETAILED DESCRIPTION

Figure 1A:
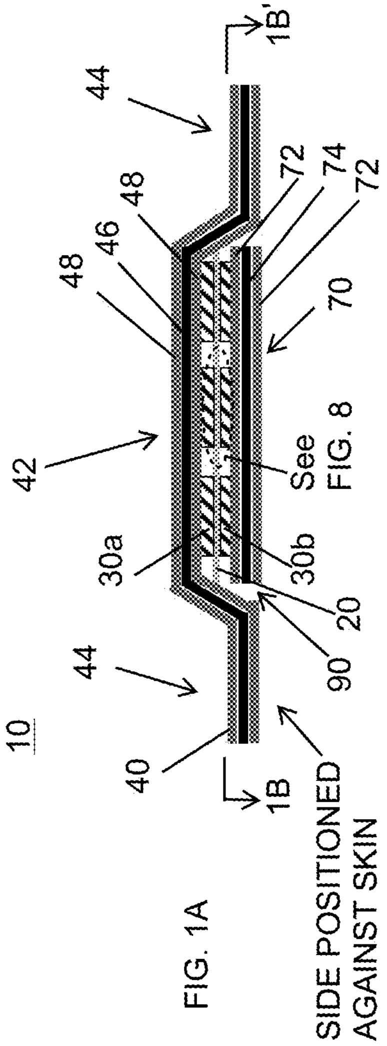
FIG. 1A is a schematic cross-sectional representation of an exemplary treatment assembly as disclosed herein.

This application describes exemplary treatment assemblies that can be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise.

As used herein, the term herein "conductive adhesive or gel" should be understood to mean "conductive adhesive or conductive gel." Further, the term "conductive gel" should be understood to include conductive hydrogel.

Existing electrode assemblies for providing TTFields are constructed with dielectric (ceramic) materials oriented toward the skin of a subject, often spaced from the skin by only soft adhesive materials (e.g., a conductive hydrogel). Therefore, when current is provided through these dielectric materials, the skin of the subject can quickly heat up and may remain at an elevated temperature under the assembly even following application of the TTFields treatment. The localized delivery of current through the dielectric materials can also lead to uneven distribution of current, resulting in uneven heating across the footprint of the electrode assembly and, in some cases, current spikes and/or hot spots. Further, existing electrode assemblies have large, rigid circuit boards that reduce user comfort.

Disclosed herein are apparatuses, systems, and methods that can address one or more of the limitations of existing electrode assemblies for providing TTFields. For example, it is contemplated that the disclosed apparatuses, systems, and methods can limit heating of the skin of a subject and/or provide faster cooling of the skin of the subject, both during and following application of TTFields. As another example, it is contemplated that the disclosed apparatuses, systems, and methods can decrease the current density at the interfaces between dielectric material and soft adhesive/gel material. It is further contemplated that the disclosed apparatuses, systems, and methods can provide for a more uniform distribution of current throughout the footprint of the device. As yet another example, it is contemplated that the disclosed apparatuses, systems, and methods can make use of treatment assemblies having circuit boards of smaller size (and area) than existing electrode assemblies, thereby improving the flexibility of the treatment assemblies.

Figure 1B:
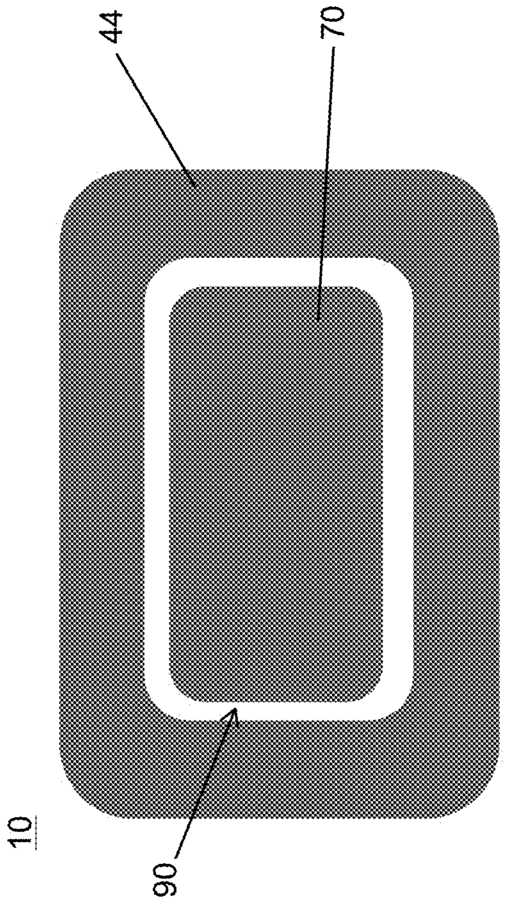
FIG. 1B is a sectional view of the treatment assembly of FIG. 1A, taken at section line 1B-1B'.
Figure 2:
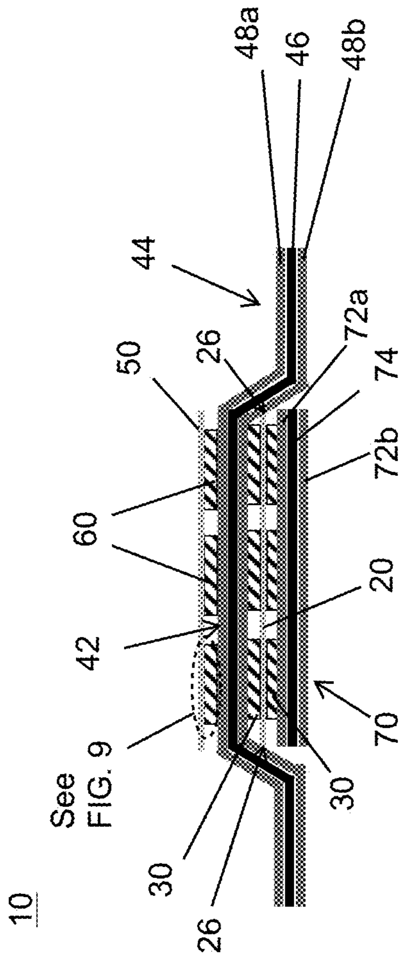
FIG. 2 is a schematic cross-sectional representation of an exemplary treatment assembly as disclosed herein.
Figure 8:
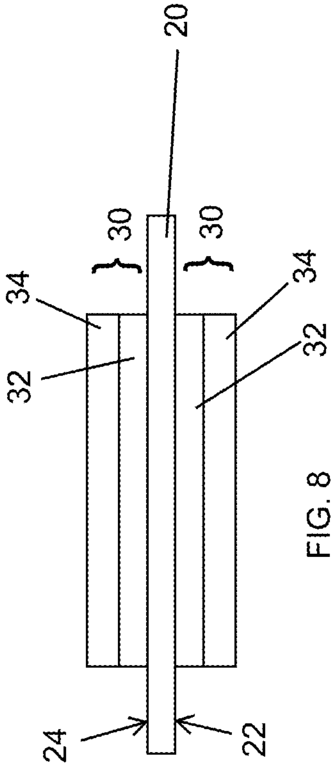
FIG. 8 is an isolated, close-up cross-section representation of a portion of the treatment assembly of FIG. 1.

Referring to FIGS. 1-5 and 8-9, a treatment assembly 10 can comprise a circuit board 20, a plurality of electrode elements 30, and a cover 40. As shown in FIG. 8, the circuit board 20 can have a skin-facing side 22 and an opposing outer side 24. As shown in FIG. 2, the circuit board 20 can have a perimeter 26. Optionally, the circuit board 20 can be planar or generally planar. In exemplary aspects, the circuit board 20 can be a printed circuit board. In some aspects, the circuit board 20 can be a flex circuit as is known in the art. However, it is contemplated that other circuit structures can be used. For example, and without limitation, it is contemplated that the circuit board 20 can comprise a thin-film circuit, such as, for example and without limitation, the thin-film circuits and flexible microcircuits manufactured by CIRTEC MEDICAL CORP. (Lowell, MA).

As shown in FIG. 8, each electrode element 30 of the plurality of electrode elements can comprise a metal layer 32 and, optionally, a capacitive layer 34. It is contemplated that the capacitive layer 34 can comprise a dielectric material, such as, for example and without limitation, a ceramic material or a high dielectric polymer. In exemplary aspects, each electrode element 30 can be electrically coupled to the circuit board 20 via the metal layer 32 of the electrode element. At least a first electrode element (e.g., electrode element 30*a* of FIG. 1A) of the plurality of electrode elements 30 can be positioned on the outer side 24 of the circuit board 20. Optionally, at least two of the plurality of electrode elements are positioned on the outer side 24 of the circuit board 20. In exemplary aspects, the cover 40 can have a first portion 42 and a second portion 44. As shown in FIGS. 1A and 2-6, the first portion 42 can be disposed over the first electrode element and the outer side 24 of the circuit board 20. In these aspects, the first portion 42 of the cover 40 can contact the first electrode element. In further aspects, the second portion 44 of the cover 40 can be positioned radially outside of the perimeter 26 of the circuit board 20. For example, when the electrodes 30, the circuit board 20, and the first portion 42 of the cover are stacked along an axis, it is contemplated that the second portion 44 of the cover can extend radially outward from the axis such that the second portion extends beyond the perimeter 26 of the circuit board 20. Thus, it is contemplated that the footprint of the cover 40 can be greater than the footprint of the circuit board 20, with the circuit board enclosed within a space defined between the skin facing side of the cover 40 and the skin of the subject.

In further aspects, the cover 40 can comprise a layer of anisotropic material 46 (that is, anisotropic with respect to thermal conductivity and/or electrical conductivity, as further discussed below) and at least one conductive adhesive or gel layer 48. Although shown as comprising multiple adhesive layers 48, it is contemplated that the cover 40 can comprise a single adhesive layer 48 such that the layer of anisotropic material 46 defines an outer surface of the cover. In exemplary aspects, any contact between the cover 40 and an electrode element 30 of the plurality of electrode elements occurs by contact with a conductive adhesive or gel layer 48 of the at least one conductive adhesive or gel layer. For example, in some aspects, a first conductive adhesive or gel layer 48 of the at least one conductive adhesive or gel layer can at least partially (optionally, entirely) define a skin-facing surface of the first portion 42 of the cover 40. In these aspects, it is contemplated that an outer surface of at least one electrode element 30 (optionally, outer surfaces of at least two electrode elements 30) can contact the skin-facing surface of the first portion 42 of the cover 40. It is further contemplated that the outer surface of the at least one electrode element 30 can be defined by the capacitive layer 34 of the electrode element. In exemplary aspects, the layer of anisotropic material 46 of the cover 40 can comprise graphite (discussed below). Optionally, in further exemplary aspects, the cover 40 can comprise a stack having two conductive adhesive or gel layers 48 (e.g., two distinct layers that are independent of one another), and the layer of anisotropic material 46 of the cover can be positioned between the two conductive adhesive or gel layers (such that the layer of anisotropic material is sandwiched between the two conductive adhesive or gel layers).

Figure 4:
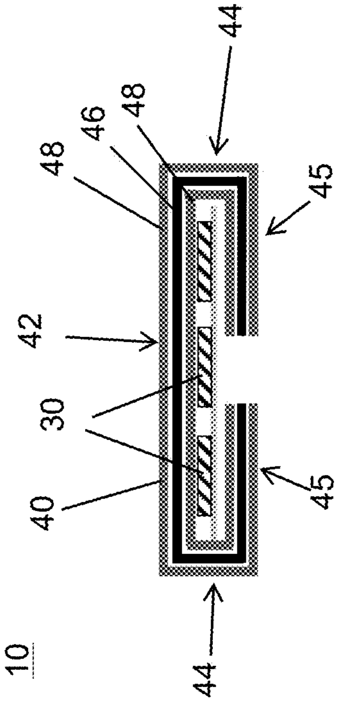
FIG. 4 is a schematic cross-sectional representation of an exemplary treatment assembly as disclosed herein.

In some exemplary aspects, and as shown in FIG. 4, it is contemplated that each electrode element 30 of the plurality of electrode elements can be positioned on the outer side 24 of the circuit board 20 and in contact with the cover 40.

In further exemplary aspects, it is contemplated that the treatment assembly 10 does not include electrode elements positioned on the skin-facing side 22 of the circuit board 20.

In additional aspects, and with reference to FIGS. 1A, 2-3, 5, and 8, at least a second electrode element **30*b* of the plurality of electrode elements 30 can be positioned on the skin-facing side 22 of the circuit board 20**.

Figure 5:
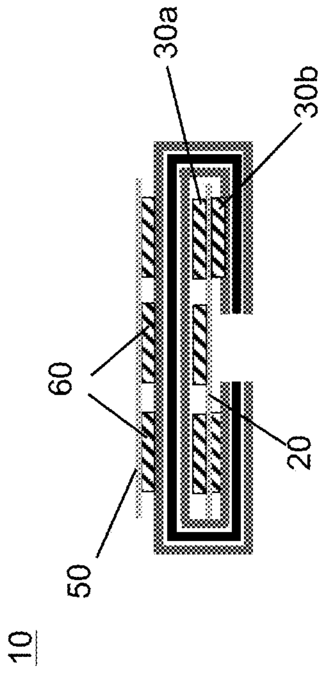
FIG. 5 is a schematic cross-sectional representation of an exemplary treatment assembly as disclosed herein.

In exemplary aspects, and with reference to FIGS. 4-5, the cover 40 can further comprise a third portion 45 that underlies the circuit board 20 on the skin-facing side 22 of the circuit board. Thus, as shown in the figures, the cover 40 can wrap around the perimeter 26 of the circuit board 20, with the first portion 42 of the cover overlying the circuit board 20, the second portion 44 of the cover extending around the sides of the cover, and the third portion 45 of the cover extending under at least a portion of the circuit board 20. Although shown in FIGS. 4-5 as extending under only a portion of the circuit board 20, it is contemplated that in some embodiments the third portion 45 can extend underneath the entire footprint of the circuit board 20. Optionally, it is contemplated that the cover 40 can be a continuous structure. Alternatively, it is contemplated that the cover 40 can comprise multiple structures that are coupled together.

In further aspects, and with reference to FIG. 5, it is contemplated that at least one electrode element **30*b* of the plurality of electrode elements 30 can be positioned on the skin-facing side of the circuit board. It is further contemplated that said at least one electrode element 30*b* can contact the third portion 45 of the cover 40. Alternatively, in other aspects, and with reference to FIG. 4, the treatment assembly 10 does not include electrode elements on the skin-facing side 22 of the circuit board 20**.

Figure 3:
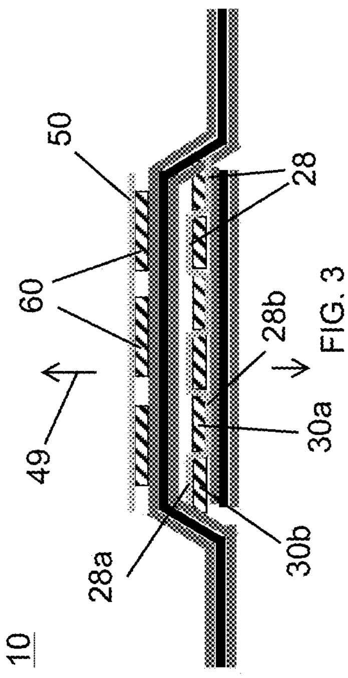
FIG. 3 is a schematic cross-sectional representation of an exemplary treatment assembly as disclosed herein.
Figure 9:
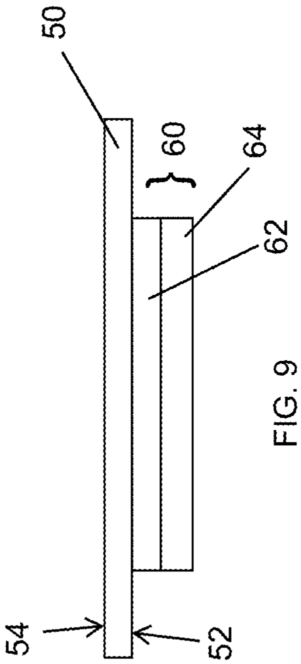
FIG. 9 is an isolated, close-up cross-section representation of a portion of the treatment assembly of FIG. 2.

In further aspects, and with reference to FIGS. 2-3 and 5, the treatment assembly 10 can further comprise a second circuit board 50 overlying the cover 40 and the circuit board 20. In these aspects, the second circuit board 50 can have a skin-facing side 52 and an opposing outer side 54 (FIG. 9). Optionally, the second circuit board 50 can be planar or generally planar. In exemplary aspects, the second circuit board 50 can be a printed circuit board. In some aspects, the second circuit board 50 can be a flex circuit as is known in the art. However, it is contemplated that other circuit structures can be used. For example, and without limitation, it is contemplated that the second circuit board 50 can comprise a thin-film circuit, such as, for example and without limitation, the thin-film circuits and flexible microcircuits manufactured by CIRTEC MEDICAL CORP. (Lowell, MA).

The treatment assembly 10 can further comprise a second plurality of electrode elements 60, with each electrode element comprising a metal layer 62 and, optionally, a capacitive layer 64 as shown in FIG. 9. It is contemplated that the capacitive layer 64 can comprise a dielectric material, such as, for example and without limitation, a ceramic material or a high dielectric polymer. The second plurality of electrode elements 60 can be coupled to the second circuit board 50 via the metal layer 62, and can be positioned on the skin-facing side 52 of the second circuit board. In these aspects, any contact between the cover 40 and an electrode element 60 of the second plurality of electrode elements occurs by contact with a second conductive adhesive or gel layer **48*b* of the at least one conductive adhesive or gel layer (with a first conductive adhesive or gel layer 48*a* positioned on an opposed side of the layer of anisotropic material 46) (FIG. 2). Each electrode element can cover a respective area, and the respective areas of the electrode elements of a plurality of elements can be summed to define a total area of the plurality of electrode elements. In exemplary aspects, the first plurality of electrode elements 30 can cooperate to define a first total area, and the second plurality of electrode elements 60** can cooperate to define a second total area that is different from the first total area.

In additional aspects, and with reference to FIG. 3, the circuit board 20 can have an oscillating profile defined by a plurality of board sections 28. For example, in these aspects, the plurality of board sections 28 can comprise at least a first board section **28*a* and a second board section 28*b* that are offset from one another, with the first board section being positioned outwardly of the second board section (moving away from the skin). Within the first board section 28*a*, at least one electrode element (e.g., electrode element 30*b* as shown in FIG. 3) of the plurality of electrode elements 30 can be positioned on the skin-facing side 22 of the circuit board 20. Within the second board section 28*b*, at least one electrode element (e.g., electrode element 30*a* of the plurality of electrode elements) can be positioned on the outer side 24 of the circuit board 20. In exemplary aspects, the oscillating profile can be defined by the plurality of board sections moving along a transverse axis, which can be perpendicular to a first axis 49 along which the circuit board and first portion of the cover are stacked (i.e., the first axis is moving toward and away from the skin). Thus, in these aspects, it is contemplated that the first and second board sections 28*a*, 28*b* can be offset from one another along the first axis. Optionally, it is contemplated that the oscillating profile can comprise an alternating pattern of board sections corresponding to the first and second board sections 28*a*, 28*b*. In these aspects, it is contemplated that the plurality of electrode elements 30 can be arranged in a generally planar configuration, with the plurality of electrode elements including electrodes on the inner side of the board sections corresponding to the first board section 28*a* and electrodes on the outer side of the board sections corresponding to the second board section 28*b*. Accordingly, the embodiment of FIG. 3 with the oscillating profile for the circuit board may be viewed as an alternative construct of the FIG. 2 embodiment. In both cases, the lower circuit board (closer to the skin) directs heat generated from the electrode elements both in an upward direction and a downward direction. In the FIG. 2** embodiment, the lower circuit board (closer to the skin) has a double layer of electrode elements wherein each areal location is directing heat in two directions, both up (away from the skin) and down (toward the skin). In the FIG.

3 embodiment, the lower circuit board (closer to the skin) has a single layer of electrode elements wherein each areal location is directing heat in only one direction, either up (away from the skin) or down (toward the skin). Advantageously, the FIG. 3 embodiment enables a thinner assembly on the skin, which adds to patient comfort by providing both a lighter assembly and a more flexible assembly on the skin.

In further exemplary aspects, and with reference to FIGS. 1A-3, the treatment assembly 10 can further comprise a base structure 70. In these aspects, the base structure 70 can be configured to contact a portion of the skin of the subject. As such, the base structure 70 can be positioned under the skin-facing side 22 of the circuit board 20 (spaced from the circuit board in a direction toward the skin) such that the first portion 42 of the cover 40 overlies the base structure 70. In further aspects, the base structure 70 can comprise at least one conductive adhesive or gel layer 72. In exemplary aspects, at least one electrode element (e.g., electrode element 30*b* as shown in FIGS. 1A and 3) of the plurality of electrode elements is positioned on the skin-facing side 22 of the circuit board 20. Optionally, said at least one electrode element contacts a conductive adhesive or gel layer 72 of the at least one conductive adhesive or gel layer of the base structure 70. Optionally, in further aspects, the base structure can comprise a layer of anisotropic material 74. In exemplary aspects, the layer of anisotropic material of the base layer 70 can comprise graphite (discussed below. Optionally, in exemplary aspects, the base structure 70 can comprise a stack having two conductive adhesive or gel layers 72*a,b* (e.g., distinct layers that are independent of one another) and a layer of anisotropic material 74 positioned between the two conductive adhesive or gel layers (FIG. 2).

As shown in FIG. 1B, when a base structure 70 is provided, it is contemplated that a circumferential gap 90 can be defined between the base structure 70 and the second portion 44 of the cover 40, with both the base structure and the second portion of the cover being in contact with the body of the subject.

Treatment Assemblies without Electrode Elements Secured to Circuit Boards

Figure 6:
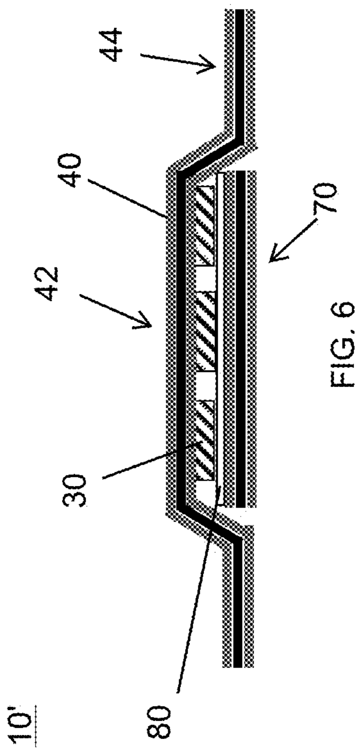
FIG. 6 is a schematic cross-sectional representation of an exemplary treatment assembly as disclosed herein.

In an alternative embodiment of the treatment assembly, and with reference to FIG. 6, it is contemplated that the treatment assembly 10' can optionally omit a circuit board. In these aspects, the treatment assembly 10' can comprise a plurality of electrode elements 30, with each electrode element comprising a metal layer 32 and, optionally, a capacitive layer 34 (FIG. 8). The treatment assembly 10' can further comprise a cover 40 having a first portion 42 and a second portion 44. The first portion 42 can be disposed over the plurality of electrode elements 30, and the first portion of the cover can have a skin-facing side that contacts at least a first electrode element of the plurality of electrode elements 30. The second portion 44 can be positioned outwardly (optionally, radially outwardly from the axis along which the electrode elements 30 and the first portion of the cover are stacked) of an area occupied by the plurality of electrode elements 30. Optionally, the treatment assembly 10' can further comprise a base structure 70, which can be positioned under the skin-facing side of the first portion 42 of the cover 40 such that the first portion of the cover overlies the base structure. In exemplary aspects, the base structure 70 comprises at least one conductive adhesive or gel layer 72 as further disclosed herein.

In further aspects, the treatment assembly 10' can further comprise a thermal barrier layer 80 that is positioned between the base structure 70 and the first electrode element. The thermal barrier layer may be, for example, one of many types of foam (open porosity, closed porosity, any percentage of open or closed porosity), including polyurethane foams, polyether foam, polyester foam, polyolefin foams, etc. In these aspects, it is contemplated that the metal layers of the electrode elements 30 can be electrically coupled to a wire, a flex circuit, or other suitable electrical connection structure that permits delivery of AC voltage to the electrode elements. It is contemplated that a thermal barrier layer 80 can be provided to ensure that the heat from the electrodes is deflected away from the skin.

In still further aspects, the cover 40 can comprise a layer of anisotropic material 46 and at least one conductive adhesive or gel layer 48 as further disclosed herein. It is contemplated that any contact between the cover 40 and an electrode element of the plurality of electrode elements 30 occurs by contact with a conductive adhesive or gel layer 48 of the at least one conductive adhesive or gel layer of the cover 40. It is further contemplated that the electrode elements 30 of the treatment assembly 10' need not include a capacitive layer 34.

Systems and Methods of Using the Treatment Assemblies

Figure 7:
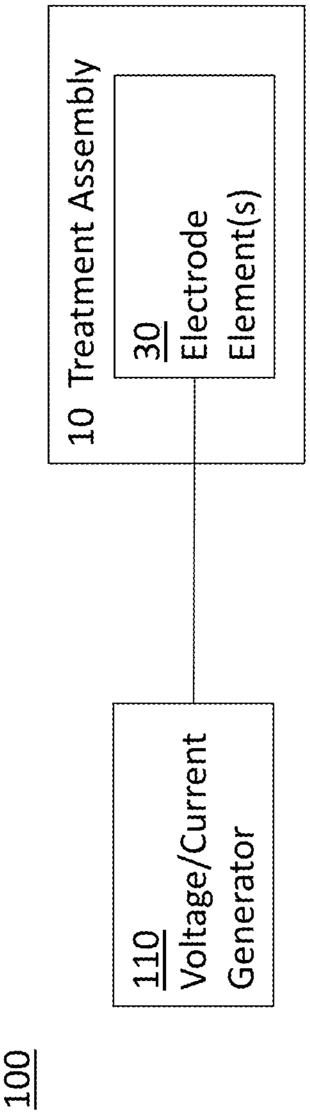
FIG. 7 is a block diagram of a system comprising a voltage/current generator and at least one treatment assembly as disclosed herein.

With reference to FIG. 7, a system 100 for applying TTFields can comprise a treatment assembly 10, 10' as disclosed herein and an alternating-current (AC) voltage generator 110 coupled to the treatment assembly. Although not shown, it is contemplated that a lead or other electrical connector or cable can supply an AC voltage (directly or indirectly) from the AC voltage generator 110 to the electrode element(s) to generate the TTFields when the electrode assembly 100 is affixed or otherwise coupled to the subject's body for treatment. In exemplary aspects, it is contemplated that the metal layers of all or a portion of the electrode elements of a given treatment assembly can be wired together (e.g., using wires, traces on a flex circuit, etc.) to a lead. The lead can supply the AC voltage from the AC voltage generator 110 to the electrode elements 30 to generate the TTFields when the treatment assembly 10 is affixed to the subject's body for treatment (as described herein).

In use, a method of providing TTFields can comprise positioning a treatment assembly 10, 10' on skin of a subject and generating, by the plurality of electrode elements, electric fields. As can be understood, the TTFields can be generated by the electrode elements in response to delivery of an AC voltage by voltage generator 110 as further disclosed herein.

The method of applying TTFields can include positioning a first treatment assembly at a first position on or in the subject's body. For example, the treatment assembly can be positioned on the subject's skin facing a target region (e.g., a tumor).

The method can also include positioning a second treatment assembly at a second position in or on the subject's body. For example, the second treatment assembly can be positioned on the subject's skin at a second position facing the target region, but on an opposing side of the target region from the first position.

The method can further include applying an alternating voltage between the first treatment assembly and the second treatment assembly. The applying is performed after positioning the first electrode assembly and the second electrode assembly.

In some embodiments, the frequency of the alternating voltage is between 50 kHz and 1 MHz, or between 100 kHz and 500 kHz. It is contemplated that the AC voltage generator 110 can be controlled by a controller (not shown), which can optionally use temperature measurements to control the amplitude of the current to be delivered via the first and second treatment assemblies in order to maintain temperatures below a safety threshold (e.g., 41° C.). This can be accomplished, for example, by measuring a first temperature of a first electrode element, measuring a second temperature of a second electrode element, and controlling the applying of the alternating voltage based on the first temperature and the second temperature.

In use, it is contemplated that the disclosed treatment assemblies can allow for positioning dielectric material on an outer side of a circuit board and/or thermal barrier within the assembly, thereby directing heat away from the skin and allowing for faster cooling of the skin. Additionally, it is contemplated that the anisotropic material within the cover can help dissipate heat from the area of skin under the electrode elements both to areas of skin beyond the area under the electrode elements and also to the ambient environment. Further, it is contemplated that the positioning of electrode elements on the outer side of the circuit board or thermal barrier can reduce the risk of injury in the event of a rip in the skin contact layers (to prevent metal from directly contacting the skin).

It is further contemplated that the use of the disclosed cover and/or base structures, which allow for positioning of electrode elements at multiple layers within the assembly, can increase the amount of Z-direction interaction (in the direction moving toward and away from the skin) between the electrode elements (dielectric layers) and the conductive adhesive or gel layers, thereby decreasing current density and allowing for a more consistent distribution of current and heat throughout the footprint of the assembly. It is still further contemplated that the improved distribution of current and heat can allow for the use of smaller and/or more flexible treatment assemblies, which can optionally eliminate or reduce the size of rigid circuit boards.

In further aspects, it is contemplated that the relative areas and other properties of the cover and base structure can be selectively modified to adjust the properties of the TTFields that are generated by the electrode elements within the treatment assemblies. For example, it is contemplated that the electric field gradient can be modified by changing the relative areas of the cover and base structure.

Exemplary Anisotropic and Conductive Adhesive or Gel Layers

In exemplary aspects, it is contemplated that within the cover 40 and/or base structure 70, the layers of anisotropic material and the conductive adhesive or gel layers can define respective peripheral edges that are aligned or substantially aligned with one another to avoid or limit hotspots of high current, temperature, electric fields, etc. For example, it is contemplated that the footprint of the layers of anisotropic material can correspond or substantially correspond to the perimeter of adjoining conductive adhesive or gel layers (i.e., the outer edges of the layers can be generally aligned with each other).

In exemplary aspects, it is contemplated that the layers of anisotropic material can comprise sheets that have opposing faces. Each anisotropic sheet can have a first thermal conductivity in a direction that is perpendicular to a front face (facing the skin), and thermal conductivity of the sheet in directions that are parallel to the front face can be more than two times higher than the first thermal conductivity. In some preferred embodiments, the thermal conductivity of the sheet in directions that are parallel to the front face can be more than ten times higher than the first thermal conductivity. Such sheets can also be anisotropic in another respect. More specifically, the sheet can have a first resistance in a direction that is perpendicular to the front face, and the resistance of the sheet in directions that are parallel to the front face can be less than half of the first resistance. In some embodiments, the resistance of the sheet in directions that are parallel to the front face can be less than 10% of the first resistance.

In some embodiments, one or both of the disclosed layers of anisotropic material 46, 74 can be a sheet of a synthetic graphite, such as pyrolytic graphite or graphitized polymer film (e.g., graphitized polyimide). In other embodiments, the anisotropic material can be graphite foil made from compressed high purity exfoliated mineral graphite. In other embodiments, the anisotropic material can be pyrolytic carbon. Other embodiments can utilize sheets of other conducting materials with anisotropic properties. In some embodiments (e.g., when the sheet of anisotropic material is a sheet of pyrolytic graphite), the sheet of anisotropic material is nonmetallic.

In various aspects, and as further described herein, the conductive adhesive or gel layers 48, 72 disclosed herein can comprise a conductive adhesive composite, a hydrogel, or other suitable conductive material.

In some embodiments, at least the innermost conductive adhesive or gel layer of the cover 40 and/or base structure 70 can comprise hydrogel that covers the entire front face of an adjoining layer of anisotropic material. For example, the innermost conductive adhesive or gel layers can function as skin contact layers that are the same size or larger than the sheet of anisotropic material. Optionally, in these embodiments, the hydrogel can have a thickness between 50 μm and 2000 μm.

In other embodiments, at least the innermost conductive adhesive or gel layer of the cover 40 and/or base structure 70 can comprise a conductive adhesive composite.

In alternative embodiments, a different conductive material (e.g., conductive grease, conductive tape, etc.) can be used as one of the conductive adhesive or gel layers.

As discussed above, it is contemplated that one or more of the conductive adhesive or gel layers 48, 72 disclosed herein can comprise conductive adhesive composites (described further below) rather than hydrogel. In exemplary aspects, the conductive adhesive composite can comprise a dielectric material and conductive particles dispersed within the dielectric material. In some embodiments, at least a portion of the conductive particles can define a conductive pathway through a thickness of the conductive adhesive composite. In some embodiments, it is contemplated that the conductive particles can be aligned in response to application of an electric field such that the conductive particles undergo electrophoresis. In some aspects, the dielectric material of the electrode assemblies is a polymeric adhesive. Optionally, in these aspects, the polymeric adhesive can be an acrylic adhesive. In some aspects, the conductive particles can comprise carbon. Optionally, in these aspects, the conductive particles can comprise graphite powder. Additionally, or alternatively, the conductive particles can comprise carbon flakes. Additionally, or alternatively, the conductive particles can comprise carbon granules. Additionally, or alternatively, the conductive particles can comprise carbon nanotubes. Additionally, or alternatively, the conductive particles can comprise carbon black powder. Additionally, or alternatively, the conductive particles can comprise carbon microcoils. In further aspects, the conductive adhesive composite further comprises a polar material (e.g., a polar salt). The polar salt can be a quaternary ammonium salt, such as a tetra alkyl ammonium salt. Exemplary conductive adhesive composites, as well as methods for making such conductive adhesive composites, are disclosed in U.S. Pat. Nos. 8,673,184 and 9,947,432, which are incorporated herein by reference for all purposes. In exemplary aspects, the conductive adhesive composite can be a dry carbon/salt adhesive, such as the OMNI-WAVE' adhesive compositions manufactured and sold by FLEXCON® (Spencer, MA, USA); or products such as ARcare® 8006 electrically conductive adhesive composition manufactured and sold by Adhesives Research, Inc. (Glen Rock, PA, USA. In further exemplary aspects, it is contemplated that the conductive adhesive composite can comprise a layer of an electrically conductive adhesive, such as for example, from use (by removal of the transfer film layer) of Electrically Conductive Adhesive Transfer Tape 9712 or Electrically Conductive Adhesive Transfer Tape 9713 (both manufactured by 3M).

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A treatment assembly comprising:

- a circuit board having a skin-facing side and an opposing outer side, wherein the circuit board has a perimeter;
- a plurality of electrode elements comprising a metal layer and, optionally, a capacitive layer, the electrode elements being coupled to the circuit board via the metal layer, wherein at least a first electrode element of the plurality of electrode elements is positioned on the outer side of the circuit board; and
- a cover having:
  - a first portion that is disposed over the first electrode element and the outer side of the circuit board, wherein the first portion of the cover contacts the first electrode element; and
  - a second portion that is positioned radially outside of the perimeter of the circuit board,
- wherein the cover comprises a layer of anisotropic material and at least one conductive adhesive or gel layer, and
- wherein any contact between the cover and an electrode element of the plurality of electrode elements occurs by contact with a conductive adhesive or gel layer of the at least one conductive adhesive or gel layer, and
- wherein the layer of anisotropic material comprises a sheet of anisotropic material having a front face and a rear face, wherein:
  - the sheet having a first thermal conductivity in a direction that is perpendicular to the front face, and thermal conductivity of the sheet in directions that are parallel to the front face is more than two times higher than the first thermal conductivity, or
  - the sheet has a first resistance in a direction that is perpendicular to the front face, and resistance of the sheet in directions that are parallel to the front face is less than half of the first resistance.

Aspect 2: The treatment assembly of aspect 1, wherein at least two of the plurality of electrode elements are positioned on the outer side of the circuit board and in contact with the cover.

Aspect 3: The treatment assembly of any one of the preceding aspects, wherein each electrode element of the plurality of electrode elements is positioned on the outer side of the circuit board and in contact with the cover.

Aspect 4: The treatment assembly of any one of the preceding aspects, wherein the treatment assembly does not include electrode elements positioned on the skin-facing side of the circuit board.

Aspect 5: The treatment assembly of any one of aspects 1-2, wherein at least a second electrode element of the plurality of electrode elements is positioned on the skin-facing side of the circuit board.

Aspect 6: The treatment assembly of any one of the preceding aspects, wherein the cover is a continuous structure.

Aspect 7: The treatment assembly of any one of the preceding aspects, wherein the cover further comprises a third portion that underlies the circuit board on the skin-facing side of the circuit board.

Aspect 8: The treatment assembly of aspect 7, wherein at least one electrode element of the plurality of electrode elements is positioned on the skin-facing side of the circuit board, and wherein said at least one electrode element contacts the third portion of the cover.

Aspect 9: The treatment assembly of any one of the preceding claims, further comprising: a second circuit board overlying the cover and the circuit board, the second circuit board having a skin-facing side and an opposing outer side; and a second plurality of electrode elements comprising a metal layer and, optionally, a capacitive layer, the electrode elements being coupled to the second circuit board via the metal layer, wherein the second plurality of electrode elements are positioned on the skin-facing side of the second circuit board, wherein any contact between the cover and an electrode element of the second plurality of electrode elements occurs by contact with a second conductive adhesive or gel layer of the at least one conductive adhesive or gel layer.

Aspect 10: The treatment assembly of aspect 9, wherein the first plurality of electrode elements cooperate to define a first total area, wherein the second plurality of electrode elements cooperate to define a second total area, and wherein the first total area is different from the second total area.

Aspect 11: The treatment assembly of any one of the preceding aspects, wherein the circuit board has an oscillating profile defined by a plurality of board sections, wherein the plurality of board sections comprises at least a first board section and a second board section that are offset from one another, wherein the first board section is positioned outwardly of the second board section, wherein within the first board section, at least one electrode element of the plurality of electrode elements is positioned on the skin-facing side of the circuit board, and wherein within the second board section, at least one electrode element of the plurality of electrode elements is positioned on the outer side of the circuit board.

Aspect 12: The treatment assembly of any one of the preceding aspects, further comprising a base structure, wherein the base structure is positioned on the skin-facing side of the circuit board such that the first portion of the cover overlies the base structure, wherein the base structure comprises a second layer of anisotropic material and at least one conductive adhesive or gel layer, and wherein the second layer of anisotropic material comprises a sheet of anisotropic material having a front face and a rear face, the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, wherein resistance of the sheet in directions that are parallel to the front face is less than half of the first resistance.

Aspect 13: The treatment assembly of aspect 12, wherein at least one electrode element of the plurality of electrode elements is positioned on the skin-facing side of the circuit board, and wherein said at least one electrode element contacts a conductive adhesive or gel layer of the at least one conductive adhesive or gel layer of the base structure.

Aspect 14: The treatment assembly of any one of aspects 12-13, wherein the second layer of anisotropic material comprises graphite.

Aspect 15: The treatment assembly of aspect 14, wherein the second layer of anisotropic material comprises synthetic graphite.

Aspect 16: The treatment assembly of aspect 12, wherein the second layer of anisotropic material of the base structure comprises pyrolytic graphite, graphitized polymer film, or graphite foil made from compressed high purity exfoliated mineral graphite.

Aspect 17: The treatment assembly of any one of aspects 12-16, wherein the base structure comprises a stack having two conductive adhesive or gel layers (e.g., two distinct, independent conductive adhesive or gel layers) and the second layer of anisotropic material positioned between the two conductive adhesive or gel layers.

Aspect 18: The treatment assembly of any one of the preceding aspects, wherein the layer of anisotropic material of the cover comprises graphite or synthetic graphite.

Aspect 19: The treatment assembly of any one of the preceding claims, wherein the layer of anisotropic material of the cover comprises pyrolytic graphite, graphitized polymer film, or graphite foil made from compressed high purity exfoliated mineral graphite.

Aspect 20: The treatment assembly of aspect 18 or 19, wherein the cover comprises a stack having two conductive adhesive or gel layers (e.g., two distinct, independent conductive adhesive or gel layers), and wherein the layer of anisotropic material of the cover is positioned between the two conductive adhesive or gel layers.

Aspect 21: A treatment assembly comprising:

a plurality of electrode elements comprising a metal layer, wherein the plurality of electrode elements occupy an area; and a cover having:

a first portion that is disposed over the plurality of electrode elements, wherein the first portion of the cover has a skin-facing side that contacts at least a first electrode element of the plurality of electrode elements; and a second portion that is positioned outwardly beyond the area occupied by the plurality of electrode elements, wherein the cover comprises a layer of anisotropic material and at least one conductive adhesive or gel layer;

a base structure, wherein the base structure is positioned on the skin-facing side of the first portion of the cover such that the first portion of the cover overlies the base structure, wherein the base structure comprises a second layer of anisotropic material and at least one conductive adhesive or gel layer; and a thermal barrier layer positioned between the base structure and the first electrode element, wherein any contact between the cover and an electrode element of the plurality of electrode elements occurs by contact with a conductive adhesive or gel layer of the at least one conductive adhesive or gel layer of the cover, and wherein the layer of anisotropic material and the second layer of anisotropic material each comprise a respective sheet of anisotropic material having a front face and a rear face, wherein:

the sheet has a first thermal conductivity in a direction that is perpendicular to the front face, and thermal conductivity of the sheet in directions that are parallel to the front face is more than two times higher than the first thermal conductivity; or the sheet has a first resistance in a direction that is perpendicular to the front face, and resistance of the sheet in directions that are parallel to the front face is less than half of the first resistance.

Aspect 22: A system comprising: a treatment assembly as in any one of aspects 1-20; and a current generator coupled to the treatment assembly.

Aspect 23: A system comprising: a treatment assembly as in aspect 22; and a current generator coupled to the treatment assembly.

Aspect 24: A treatment assembly comprising:

a circuit board having a skin-facing side and an opposing outer side, wherein the circuit board has a perimeter;

a plurality of electrode elements coupled to the circuit board, wherein at least a first electrode element of the plurality of electrode elements is positioned on the outer side of the circuit board; and a cover having:

a first portion that is disposed over the first electrode element and the outer side of the circuit board, wherein the first portion of the cover contacts the first electrode element; and a second portion that is positioned radially outside of the perimeter of the circuit board, wherein the cover comprises a layer of anisotropic material and at least one conductive adhesive or gel layer, and wherein the layer of anisotropic material comprises a sheet of anisotropic material having a front face and a rear face, wherein:

the sheet has a first thermal conductivity in a direction that is perpendicular to the front face, and thermal conductivity of the sheet in directions that are parallel to the front face is more than two times higher than the first thermal conductivity, or the sheet has a first resistance in a direction that is perpendicular to the front face, and resistance of the sheet in directions that are parallel to the front face is less than half of the first resistance.

Aspect 25: The treatment assembly of aspect 24, wherein each electrode element of the plurality of electrode elements comprises a metal layer.

Aspect 26: The treatment assembly of aspect 24 or aspect 25, wherein each electrode element of the plurality of electrode elements comprises a dielectric layer.

Aspect 27: The treatment assembly of any one of aspects 24-26, wherein at least two of the plurality of electrode elements are positioned on the outer side of the circuit board and in contact with the cover.

Aspect 28: The treatment assembly of any one of aspects 24-27, wherein each electrode element of the plurality of electrode elements is positioned on the outer side of the circuit board and in contact with the cover.

Aspect 29: The treatment assembly of any one of aspects 24-28, wherein the treatment assembly does not include electrode elements positioned on the skin-facing side of the circuit board.

Aspect 30: The treatment assembly of any one of aspects 24-26, wherein at least a second electrode element of the plurality of electrode elements is positioned on the skin-facing side of the circuit board.

Aspect 31: The treatment assembly of any one of aspects 24-30, wherein the circuit board is planar or generally planar.

Aspect 32: The treatment assembly of any one of aspects 24-31, wherein the cover is a continuous structure.

Aspect 33: The treatment assembly of any one of aspects 24-32, wherein the cover further comprises a third portion that underlies the circuit board on the skin-facing side of the circuit board.

Aspect 34: The treatment assembly of aspect 33, wherein the cover wraps around the perimeter of the circuit board.

Aspect 35: The treatment assembly of aspect 33 or aspect 34, wherein at least one electrode element of the plurality of electrode elements is positioned on the skin-facing side of the circuit board, and wherein said at least one electrode element contacts the third portion of the cover.

Aspect 36: The treatment assembly of any one of aspects 24-35, further comprising a second circuit board overlying the cover and the circuit board, the second circuit board having a skin-facing side and an opposing outer side.

Aspect 37: The treatment assembly of aspect 36, further comprising a second plurality of electrode elements coupled to the second circuit board, wherein the second plurality of electrode elements is positioned on the skin-facing side of the second circuit board.

Aspect 38: The treatment assembly of aspect 37, wherein the second plurality of electrode elements are in contact with the cover.

Aspect 39: The treatment assembly of aspect 37 or aspect 38, wherein the first plurality of electrode elements cooperate to define a first total area, wherein the second plurality of electrode elements cooperate to define a second total area, and wherein the first total area is different from the second total area.

Aspect 40: The treatment assembly of any one of aspects 24-39, wherein the circuit board has an oscillating profile defined by a plurality of board sections, wherein the plurality of board sections comprises at least a first board section and a second board section that are offset from one another, wherein the first board section is positioned outwardly of the second board section, wherein within the first board section, at least one electrode element of the plurality of electrode elements is positioned on the skin-facing side of the circuit board, and wherein within the second board section, at least one electrode element of the plurality of electrode elements is positioned on the outer side of the circuit board.

Aspect 41: The treatment assembly of aspect 40, wherein the plurality of electrode elements are arranged in a generally planar configuration.

Aspect 42: The treatment assembly of any one of aspects 24-42, further comprising a base structure, wherein the base structure is positioned on the skin-facing side of the circuit board such that the first portion of the cover overlies the base structure, wherein the base structure comprises a second layer of anisotropic material and at least one conductive adhesive or gel layer, and wherein the second layer of anisotropic material comprises a sheet of anisotropic material having a front face and a rear face, the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, and wherein resistance of the sheet in directions that are parallel to the front face is less than half of the first resistance.

Aspect 43: The treatment assembly of aspect 42, wherein at least one electrode element of the plurality of electrode elements is positioned on the skin-facing side of the circuit board, and wherein said at least one electrode element contacts a conductive adhesive or gel layer of the at least one conductive adhesive or gel layer of the base structure.

Aspect 44: The treatment assembly of aspect 42 or aspect 43, wherein the at least one conductive adhesive or gel layer of the base structure comprises an acrylic adhesive.

Aspect 45: The treatment assembly of aspect 44, wherein the acrylic adhesive of the base structure comprises conductive particles.

Aspect 46: The treatment assembly of any one of aspects 42-45, wherein the second layer of anisotropic material comprises graphite.

Aspect 47: The treatment assembly of any one of aspect 46, wherein the second layer of anisotropic material comprises synthetic graphite.

Aspect 48: The treatment assembly of aspect 46, wherein the second layer of anisotropic material comprises a sheet of pyrolytic graphite.

Aspect 49: The treatment assembly of aspect 46, wherein the second layer of anisotropic material comprises graphite foil made from graphitized polymer film or compressed high purity exfoliated mineral graphite.

Aspect 50: The treatment assembly of any one of aspects 42-49, wherein the base structure comprises a stack having two conductive adhesive or gel layers (e.g., two distinct, independent conductive adhesive or gel layers), wherein the second layer of anisotropic material is positioned between the two conductive adhesive or gel layers.

Aspect 51: The treatment assembly of any one of aspects 24-50, wherein the at least one conductive adhesive or gel layer of the cover comprises an acrylic adhesive.

Aspect 52: The treatment assembly of aspect 51, wherein the acrylic adhesive of the cover comprises conductive particles.

Aspect 53: The treatment assembly of any one of aspects 24-52, wherein the layer of anisotropic material of the cover comprises graphite.

Aspect 54: The treatment assembly of aspect 53, wherein the layer of anisotropic material of the cover comprises synthetic graphite.

Aspect 55: The treatment assembly of aspect 53, wherein the layer of anisotropic material of the cover comprises a sheet of pyrolytic graphite.

Aspect 56: The treatment assembly of aspect 53, wherein the layer of anisotropic material of the cover comprises graphitized polymer film or graphite foil made from compressed high purity exfoliated mineral graphite.

Aspect 57: The treatment assembly of any one of aspects 51-56, wherein the cover comprises a stack having two conductive adhesive or gel layers (e.g., two distinct, independent conductive adhesive or gel layers) and a layer of anisotropic material positioned between the two conductive adhesive or gel layers.

Aspect 58: A system comprising: a treatment assembly as in any one of aspects 24-57; and a current generator coupled to the treatment assembly.

Aspect 59: A method comprising: positioning a first treatment assembly as in any one of aspects 1-20 on skin of a subject; positioning a second treatment assembly at a second position on the subject; and applying an alternating voltage between the first treatment assembly and the second treatment assembly.

Aspect 60: A method comprising: positioning a first treatment assembly as in aspect 21 on skin of a subject; positioning a second treatment assembly at a second position on the subject; and applying an alternating voltage between the first treatment assembly and the second treatment assembly.

Aspect 61: A method comprising: positioning a first treatment assembly as in any one of aspects 24-57 on skin of a subject; positioning a second treatment assembly at a second position on the subject; and applying an alternating voltage between the first treatment assembly and the second treatment assembly.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A treatment assembly for positioning on skin of a subject, the treatment assembly comprising:
- a circuit board having a skin-facing side configured to face the skin of the subject, and an opposing, outer side configured to face away from the skin of the subject, wherein the circuit board has a perimeter;
- a plurality of electrode elements, each electrode element of the plurality of electrode elements comprising a metal layer coupled to the circuit board, wherein at least a first electrode element of the plurality of electrode elements is positioned on the outer side of the circuit board; and
- a cover comprising a layer of anisotropic material and at least one conductive adhesive or gel layer, the cover having:
  - a first portion that is disposed over the first electrode element and the outer side of the circuit board, wherein the first portion of the cover contacts the first electrode element, wherein the first portion of the cover comprises respective portions of each of the layer of anisotropic material and the at least one conductive adhesive or gel layer; and
  - a second portion that is positioned radially outside of the perimeter of the circuit board,
- wherein any contact between the cover and an electrode element of the plurality of electrode elements occurs by contact with a conductive adhesive or gel layer of the at least one conductive adhesive or gel layer, and
- wherein the layer of anisotropic material comprises a sheet of anisotropic material having a front face and a rear face, wherein:
  - the sheet has a first thermal conductivity in a direction that is perpendicular to the front face, and thermal conductivity of the sheet in directions that are parallel to the front face is more than two times higher than the first thermal conductivity, or
  - the sheet has a first resistance in a direction that is perpendicular to the front face, and resistance of the sheet in directions that are parallel to the front face is less than half of the first resistance.

2. The treatment assembly of claim 1, wherein each electrode element of the plurality of electrode elements is positioned on the outer side of the circuit board and in contact with the cover.

3. The treatment assembly of claim 1, wherein the treatment assembly does not include electrode elements positioned on the skin-facing side of the circuit board.

4. The treatment assembly of claim 1, wherein at least a second electrode element of the plurality of electrode elements is positioned on the skin-facing side of the circuit board.

5. The treatment assembly of claim 1, wherein the cover is a continuous structure.

6. The treatment assembly of claim 1, wherein the cover further comprises a third portion that underlies the circuit board on the skin-facing side of the circuit board.

7. The treatment assembly of claim 6, wherein at least a second electrode element of the plurality of electrode elements is positioned on the skin-facing side of the circuit board, and wherein the second electrode element contacts the third portion of the cover.

8. The treatment assembly of claim 1, wherein the plurality of electrode elements comprises a first plurality of electrode elements, wherein the treatment assembly further comprises:
- a second circuit board overlying the cover and the circuit board, the second circuit board having a skin-facing side and an opposing outer side; and
- a second plurality of electrode elements, each electrode element of the second plurality of electrode elements comprising a metal layer coupled to the second circuit board, wherein the second plurality of electrode elements are positioned on the skin-facing side of the second circuit board,
- wherein any contact between the cover and an electrode element of the second plurality of electrode elements occurs by contact with a second conductive adhesive or gel layer of the at least one conductive adhesive or gel layer.

9. The treatment assembly of claim 8, wherein the first plurality of electrode elements cooperate to define a first total area, wherein the second plurality of electrode elements cooperate to define a second total area, and wherein the first total area is different from the second total area.

10. The treatment assembly of claim 1, wherein the circuit board has an oscillating profile defined by a plurality of board sections, wherein the plurality of board sections comprises at least a first board section and a second board section that are offset from one another, wherein the first board section is positioned outwardly of the second board section, wherein within the first board section, at least one electrode element of the plurality of electrode elements is positioned on the skin-facing side of the circuit board, and wherein within the second board section, at least one electrode element of the plurality of electrode elements is positioned on the outer side of the circuit board.

11. The treatment assembly of claim 1, further comprising:
- a base structure, wherein the base structure is positioned on the skin-facing side of the circuit board such that the first portion of the cover overlies the base structure, wherein the base structure comprises a second layer of anisotropic material and at least one conductive adhesive or gel layer, and wherein the second layer of anisotropic material comprises a sheet of anisotropic material having a front face and a rear face, the sheet having a first thermal conductivity in a direction that is perpendicular to the front face, wherein thermal conductivity of the sheet in directions that are parallel to the front face is more than two times higher than the first thermal conductivity, or the sheet has a first resistance in a direction that is perpendicular to the front face, and wherein resistance of the sheet in directions that are parallel to the front face is less than half of the first resistance.

12. The treatment assembly of claim 11, wherein at least a second electrode element of the plurality of electrode elements is positioned on the skin-facing side of the circuit board, and wherein the second electrode element contacts a conductive adhesive or gel layer of the at least one conductive adhesive or gel layer of the base structure.

13. The treatment assembly of claim 11, wherein the second layer of anisotropic material comprises graphite or synthetic graphite.

14. The treatment assembly of claim 11, wherein the second layer of anisotropic material comprises pyrolytic graphite, graphitized polymer film, or graphite foil made from compressed high purity exfoliated mineral graphite.

15. The treatment assembly of claim 11, wherein the base structure comprises a stack having two conductive adhesive or gel layers, and wherein the second layer of anisotropic material is positioned between the two conductive adhesive or gel layers.

16. The treatment assembly of claim 1, wherein the layer of anisotropic material of the cover comprises graphite or synthetic graphite.

17. The treatment assembly of claim 1, wherein the layer of anisotropic material of the cover comprises pyrolytic graphite, graphitized polymer film, or graphite foil made from compressed high purity exfoliated mineral graphite.

18. The treatment assembly of claim 1, wherein the cover comprises a stack having two conductive adhesive or gel layers, and wherein the layer of anisotropic material of the cover is positioned between the two conductive adhesive or gel layers.

19. A treatment assembly for positioning on skin of a subject, the treatment assembly comprising:

a plurality of electrode elements, each electrode element of the plurality of electrode elements comprising a metal layer, wherein each electrode element of the plurality of electrode elements has a skin-facing side that is configured to face the skin of the subject and an opposing, outer side that is configured to face away from the skin of the subject, wherein the plurality of electrode elements occupy an area; and a cover comprising a first layer of anisotropic material and at least one conductive adhesive or gel layer, the cover having:

a first portion that is disposed over the plurality of electrode elements, wherein the first portion of the cover has a skin-facing side that contacts at least a first electrode element of the plurality of electrode elements, wherein the first portion of the cover comprises respective portions of each of the first layer of anisotropic material and the at least one conductive adhesive or gel layer; and a second portion that is positioned outwardly beyond the area occupied by the plurality of electrode elements;

a base structure, wherein the base structure is positioned on the skin-facing side of the first portion of the cover such that the first portion of the cover overlies the base structure, wherein the base structure comprises a second layer of anisotropic material and at least one conductive adhesive or gel layer; and a thermal barrier layer positioned between the base structure and the first electrode element, wherein any contact between the cover and an electrode element of the plurality of electrode elements occurs by contact with a conductive adhesive or gel layer of the at least one conductive adhesive or gel layer of the cover, and wherein the first layer of anisotropic material and the second layer of anisotropic material each comprise a respective sheet of anisotropic material having a front face and a rear face, wherein:

the sheet has a first thermal conductivity in a direction that is perpendicular to the front face, and thermal conductivity of the sheet in directions that are parallel to the front face is more than two times higher than the first thermal conductivity, or the sheet has a first resistance in a direction that is perpendicular to the front face, and resistance of the sheet in directions that are parallel to the front face is less than half of the first resistance.

20. A system comprising:

a treatment assembly for positioning on skin of a subject, the treatment assembly comprising:

a circuit board having a skin-facing side configured to face the skin of the subject, and an opposing, outer side configured to face away from the skin of the subject, wherein the circuit board has a perimeter;

a plurality of electrode elements, each electrode element of the plurality of electrode elements comprising a metal layer coupled to the circuit board, wherein at least a first electrode element of the plurality of electrode elements is positioned on the outer side of the circuit board; and a cover comprising a layer of anisotropic material and at least one conductive adhesive or gel layer, the cover having:

a first portion that is disposed over the first electrode element and the outer side of the circuit board, wherein the first portion of the cover contacts the first electrode element, wherein the first portion of the cover comprises respective portions of each of the layer of anisotropic material and the at least one conductive adhesive or gel layer; and a second portion that is positioned radially outside of the perimeter of the circuit board, wherein the cover comprises a layer of anisotropic material and at least one conductive adhesive or gel layer, and wherein any contact between the cover and an electrode element of the plurality of electrode elements occurs by contact with a conductive adhesive or gel layer of the at least one conductive adhesive or gel layer, and wherein the layer of anisotropic material comprises a sheet of anisotropic material having a front face and a rear face, wherein:

the sheet has a first thermal conductivity in a direction that is perpendicular to the front face, and thermal conductivity of the sheet in directions that are parallel to the front face is more than two times higher than the first thermal conductivity, or the sheet has a first resistance in a direction that is perpendicular to the front face, and resistance of the sheet in directions that are parallel to the front face is less than half of the first resistance; and a current generator coupled to the treatment assembly.

* * * * *